(12) United States Patent
Patwardhan et al.

(10) Patent No.: US 10,145,854 B2
(45) Date of Patent: Dec. 4, 2018

(54) SYSTEMS AND METHODS FOR TEST STRIPS WITH EXTENDED DYNAMIC RANGES

(71) Applicant: Polymer Technology Systems, Inc., Indianapolis, IN (US)

(72) Inventors: Aniruddha Patwardhan, Indianapolis, IN (US); Gary L. Hughes, Anderson, IN (US); William Benedict, Indianapolis, IN (US)

(73) Assignee: Polymer Technology Systems, Inc., Indianapolis, IN (US)

(*) Notice: Subject to any disclaimer, the term of this patent is extended or adjusted under 35 U.S.C. 154(b) by 0 days.

(21) Appl. No.: 14/203,189

(22) Filed: Mar. 10, 2014

(65) Prior Publication Data

US 2014/0255960 A1 Sep. 11, 2014

Related U.S. Application Data

(60) Provisional application No. 61/776,306, filed on Mar. 11, 2013.

(51) Int. Cl.
  *G01N 33/92* (2006.01)
  *C12Q 1/28* (2006.01)
  *G01N 33/52* (2006.01)

(52) U.S. Cl.
  CPC .............. *G01N 33/92* (2013.01); *C12Q 1/28* (2013.01); *G01N 33/521* (2013.01)

(58) Field of Classification Search
  CPC ......... G01N 33/92; G01N 33/521; C12Q 1/28
  See application file for complete search history.

(56) References Cited

U.S. PATENT DOCUMENTS

| 5,510,245 | A | 4/1996 | Magers |
| 5,527,509 | A * | 6/1996 | Gibson et al. ............... 422/402 |
| 2003/0028087 | A1 | 2/2003 | Yuzhakov et al. |
| 2010/0035245 | A1 | 2/2010 | Stiene et al. |

(Continued)

FOREIGN PATENT DOCUMENTS

| CN | 1156251 A | 8/1997 |
| EP | 0759555 A2 | 2/1997 |

OTHER PUBLICATIONS

International Search Report in co-pending PCT Application No. PCT/US14/22661 dated Jul. 9, 2014, 3 pages.

(Continued)

*Primary Examiner* — Samuel P Siefke
(74) *Attorney, Agent, or Firm* — Haynes and Boone, LLP

(57) ABSTRACT

An extended range test strip includes a simple system where the end user can determine the concentration of the analyte at high concentration with a single drop of whole blood. A single drop of blood spreads across a spreading layer and into multiple reagent stacks. Multiple reagent stacks of the test strip may be configured to test for different ranges by adding a peroxide modulator. Readings from multiple reagent stacks producing a colorimetric response may be tested simultaneously. Working from the lowest range to the highest range of reagent stacks, the first reagent stack to be less than its maximum range is considered to be the reagent stack that is producing a colorimetric response related to the actual amount of analyte in the sample.

15 Claims, 7 Drawing Sheets

(56) References Cited

U.S. PATENT DOCUMENTS

| | | | |
|---|---|---|---|
| 2011/0155590 A1* | 6/2011 | Huffstodt | G01N 27/3271 205/792 |
| 2011/0262940 A1 | 10/2011 | Hisamoto et al. | |
| 2012/0138484 A1 | 6/2012 | Bommakanti et al. | |
| 2012/0282634 A1 | 11/2012 | Hughes et al. | |

OTHER PUBLICATIONS

European Search Report dated Sep. 19, 2016 issued in parallel European patent application No. 14779788.0-1408 (7 pages).

* cited by examiner

SYSTEMS AND METHODS FOR TEST STRIPS WITH EXTENDED DYNAMIC RANGES

CROSS REFERENCE TO RELATED APPLICATION

This application claims the benefit of U.S. Provisional Patent Application No. 61/776,306 filed Mar. 11, 2013, and hereby incorporated by reference to the same extent as thought fully disclosed herein.

BACKGROUND

There are numerous assays for total cholesterol, HDL, and triglycerides that have been approved for use in quantification of the above-mentioned analytes. The dynamic range, for example, of a Roche total cholesterol assay on a Cobas Integra® 400+ is from ~4-800 mg/dL. Samples that read above 800 mg/dL are diluted from 1:1 to 1:10 on board the machine and reanalyzed and thus quantified. These assays typically use serum or plasma as sample types, are tested on an expensive clinical chemistry analyzer, and require a trained certified professional to operate.

In the Point-of-Care environment, cholesterol, HDL cholesterol, or triglyceride analyses are quantified rapidly (~2 min.) using CardioChek™ test strips. There are other Point-of-Care test systems like Cholestech's cholesterol, HDL, and triglyceride tests that also can obtain results within 10 minutes. However, the limitation for both types of test is that the dynamic ranges cannot cover samples that are very high analyte concentrations and thus either are not run due to unavailability of a dilution solution or re-run using an unapproved dilution solution giving questionable results.

SUMMARY

One embodiment of an extended range test strip includes a simple system where the end user can determine the concentration of the analyte at high concentration with a single drop of whole blood. A single drop of blood spreads across a spreading layer and into multiple reagent stacks. Multiple reagent stacks of the test strip may be configured to test for different ranges by adding a peroxide modulator. Readings from multiple reagent stacks producing a colorimetric response may be tested simultaneously. Working from the lowest range to the highest range of reagent stacks, the first reagent stack to be less than its maximum range is considered to be the reagent stack that is producing a colorimetric response related to the actual amount of analyte in the sample.

In one embodiment, a method of changing the sensitivity of an analyte test strip includes providing an analyte test strip, having a first dynamic range for an analyte and a first sensitivity and precision. The method further includes treating the analyte test strip with an amount of a peroxide modulator, wherein the treating results in the analyte test strip having a second dynamic range corresponding to the amount of the peroxide modulator added and having a second sensitivity and precision, the second sensitivity and precision approximately equal to the first sensitivity and precision. Optionally, the peroxide modulator is glutathione. In one configuration, the analyte is cholesterol. In one alternative, the analyte test strip includes 4-Amino antipyrine (4-AAP) and N,N-disubstituted aniline derivatives which produce a colorimetric response. In another alternative, the glutathione reacts with hydrogen peroxide to produce glutathione disulfide as a colorless product.

In one embodiment, a test strip having a modified sensitivity to an analyte includes a reaction layer providing for having a first dynamic range for the analyte and a first sensitivity and precision. The test strip further includes an amount of a peroxide modulator, the peroxide modulator modifying the reaction layer to have a second dynamic range corresponding to the amount of the peroxide modulator added and a second sensitivity and precision, the second sensitivity and precision approximately equal to the first sensitivity and precision. Optionally, the peroxide modulator is glutathione. In one configuration, the analyte is cholesterol. Optionally, the reaction layer includes 4-Amino antipyrine (4-AAP) and N,N-disubstituted aniline derivatives which produce a colorimetric response. In one alternative, when whole blood is added to the test strip, the glutathione reacts with hydrogen peroxide to produce glutathione disulfide as a colorless product.

In one embodiment, a multirange test strip includes a spreading layer. The multirange test strip further includes a first analyte stack and a second analyte stack, the first and second analyte stacks in fluidic communication with the spreading layer, the first and second analyte stacks having layers and reagents for testing for an analyte. The layers and reagents for testing for the analyte for the first and second analyte stacks are the same. The second stack includes a peroxide modulator; the first stack has a first dynamic range for the analyte and a first sensitivity and precision; and the second stack has a second dynamic range corresponding to a first amount of the peroxide modulator added and a second sensitivity and precision, the second sensitivity and precision approximately equal to the first sensitivity and precision. Optionally, the peroxide modulator is glutathione. In one alternative, the analyte is cholesterol. Alternatively, the layers and reagents for testing for an analyte include 4-Amino antipyrine (4-AAP) and N,N-disubstituted aniline derivatives which produce a colorimetric response. Optionally, when whole blood is added to the test strip, the glutathione reacts with hydrogen peroxide to produce glutathione disulfide. In another alternative, the first range is 100-400 mg/dL, and the second range is 400-800 mg/dL. In one embodiment, the multirange test strip further includes a third analyte stack, the third analyte stack in fluidic communication with the spreading layer. The third analyte stack has the layers and reagents for testing for the analyte, the layers and reagents for testing for the analyte for the first, second, and third stacks being the same. The third stack includes the peroxide modulator, and the third stack has a third dynamic range corresponding to a second amount of the peroxide modulator added and a third sensitivity and precision, the third sensitivity and precision approximately equal to the first sensitivity and precision. Optionally, the third range is 800-1400 mg/dL.

In one embodiment, a method of testing an analyte at a higher range using an analyte test strip configured for testing at a lower range includes adding an amount of a peroxide modulator to the analyte test strip. The method further includes adding an undiluted whole blood sample to the test strip, wherein the addition of the peroxide modulator results in the higher range. Optionally, a sensitivity and precision of the analyte test strip without the peroxide modulator is approximately equal to a sensitivity and precision of the analyte test strip with the peroxide modulator. Alternatively, the peroxide modulator is glutathione. In one alternative, the peroxide modulator does not interfere with the colorimetric reagents of the analyte test strip.

BRIEF DESCRIPTION OF THE DRAWINGS

Illustrative embodiments are described in detail below with reference to the attached drawing figures.

DETAILED DESCRIPTION OF THE DRAWINGS

Described herein are embodiments of test strips with extended dynamic ranges and methods of using them and making them.

Many different analyte test strips are available having specialized ranges for testing human blood. Polymer Technology Systems, Inc. (PTS), currently provides a cholesterol test with a dynamic range for 100-400 mg/dL. It employs 4-Amino antipyrine (4-AAP) and N,N-disubstituted aniline derivatives to produce a colorimetric response (see reaction Route a of Scheme I). The configuration of such a test strip may be modified to obtain sensitivity and precision at higher concentrations of cholesterol through the use of a peroxide scavenger-like hydroquinone in the cholesterol reaction membrane. This may not be preferable for a number of reasons. Hydroquione in the presence of hydrogen peroxide reacts with 4-Amino antipyrine (4-AAP) to produce a colorless compound (see reaction Route b of Scheme I). This reaction is faster than the coupling of 4-AAP and the N,N-disubstituted aniline derivate. This is thought to be sub-optimal but may be a valid pathway.

One limitation of the use of hydroquinone as scavenger is the side reactions that it produces that cause imperfect color development and thus leads to imprecision. Additionally, hydroquione reacts with 4-AAP, which is the starting material for the colored product, thus reducing the availability of 4-AAP for the reaction. This causes loss of accuracy (due to Le Chatelier's principle) and also leads to strip instability over time.

Figure 1:
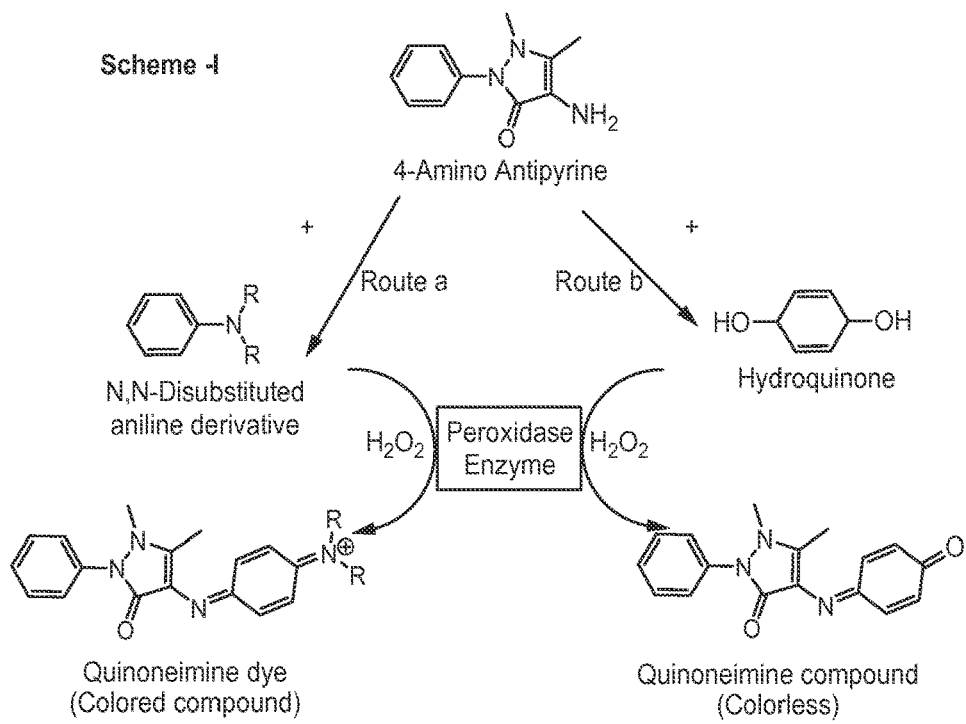
FIG. 1 shows an embodiment of a reaction pathway using hydroquinone for color development.
Figure 2:
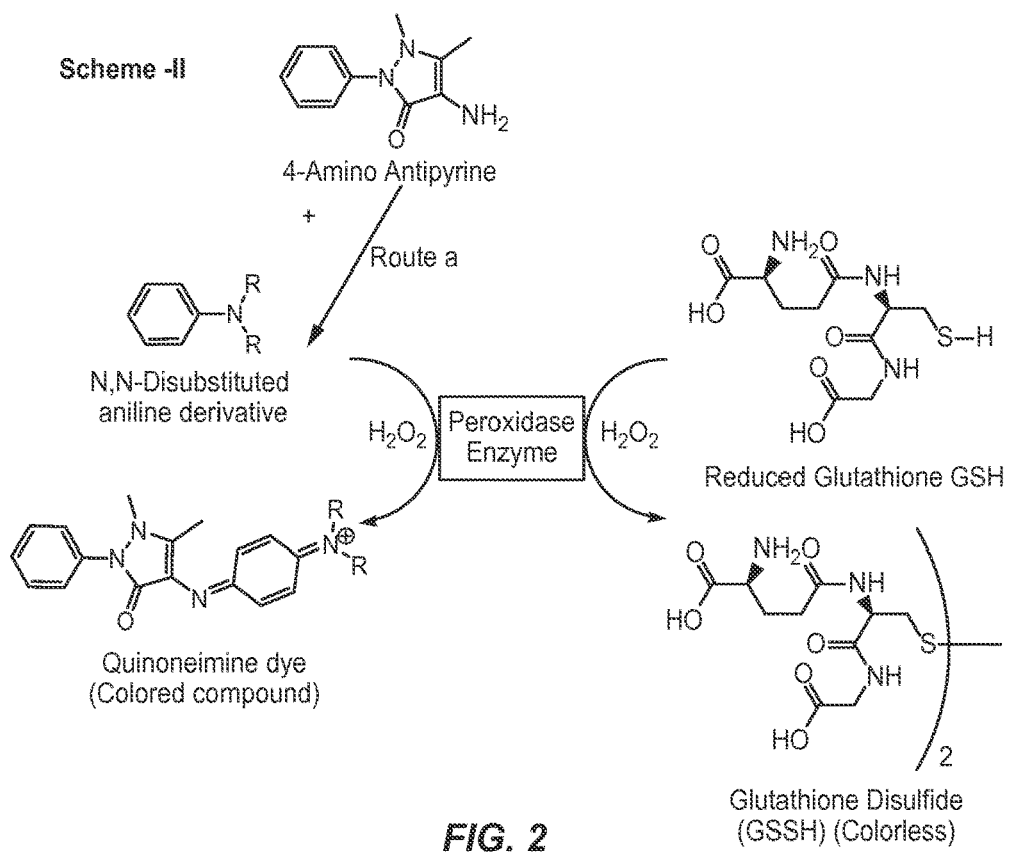
FIG. 2 shows an embodiment of a reaction pathway using glutathione for color development.

An alternative to hydrogen peroxide scavenger is the use of reduced glutathione (GSH) (referred to as a peroxide modulator). This entity reacts with hydrogen peroxide to form a dimeric species called glutathione disulfide (GSSG). An important feature of GSH is it does not react with 4-Amino antipyrine (4-AAP) (see Scheme II shown in FIG. 2), leaving it intact for reaction with a N,N-disubstituted aniline derivate. The dimerization reaction of GSH seems to be faster than the oxidative coupling of 4-AAP and a N,N-disubstituted aniline derivative as shown in "Route a" of the schemes shown in FIG. 1.

The advantage of this system is that GSH now can be used as a variable to modulate the sensitivity of the cholesterol reaction membrane. By titrating the optimal amount of GSH in the cholesterol formulation, the extent of hydrogen peroxide scavenging may be accomplished. The percent reflectance observed at a higher concentration of GSH then may be indexed to cholesterol concentrations of choosing. This allows for setting a dynamic range which can be set to higher values not typically observed in a Point-of-Care environment setting.

Figure 3:
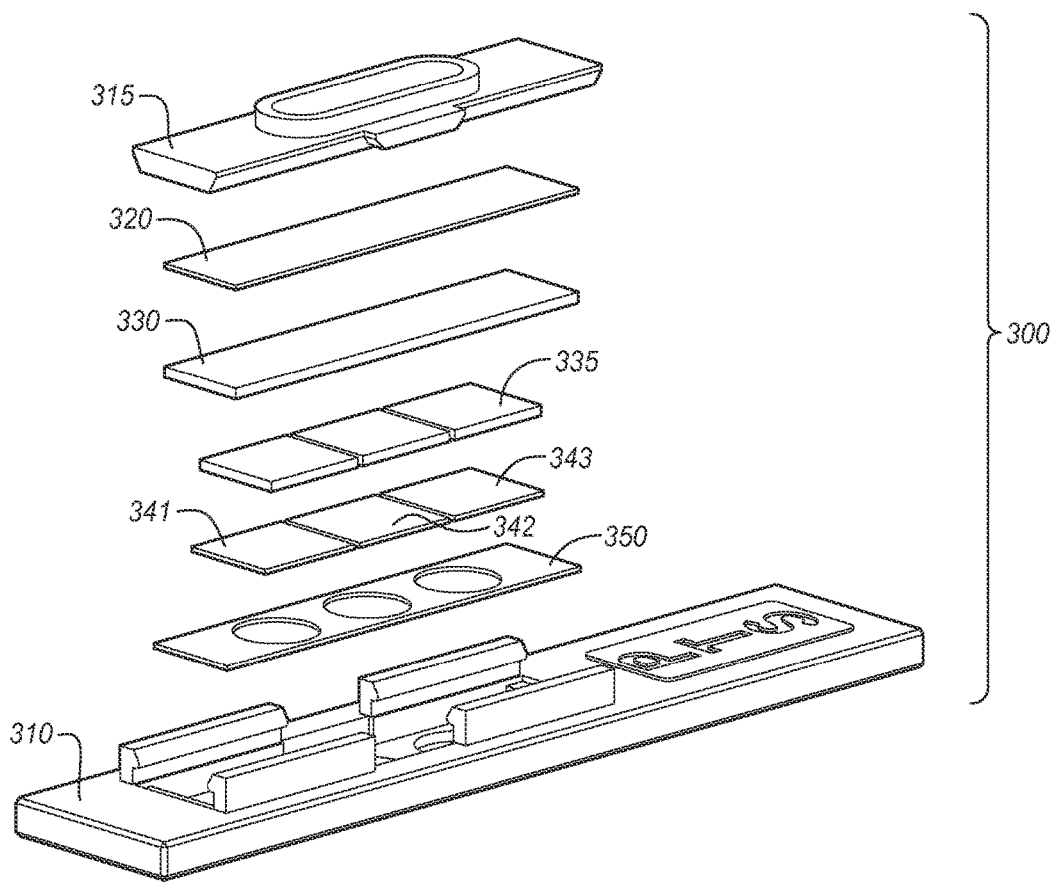
FIG. 3 shows an embodiment of a test strip employing dynamic ranges.

For example, three different cholesterol reaction membranes can be created where the dynamic range of the first membrane can be from 100-400 mg/dL, the second is from 400-800 mg/dL, and the third is from 800-1400 mg/dL, as shown in FIG. 3. FIG. 3 shows an embodiment of a test strip 300. Test strip 300 includes a base 310 and a cap 315 that make up the holder portion of the strip. Test strip 300 includes multiple layers 320, 330, 335 that may perform various separation and processing steps related to the analyte being measured. In some configurations, layer 320 is a spreading layer; layer 330 is a red blood cell separation layer; and layer 335 is a secondary blood separation layer, a blank layer, or an analyte-specific layer.

Many different configurations of the layers will occur to one skilled in the art in light of this disclosure. Various membranes may be utilized for spreading layer 320, including but not limited to Petex. Layers 330 and 335 may be blood separation and secondary blood separation layers, including D-23 Brosilicate glass fiber with phaselous vulgaris lectins and Cytosep (0.15% Dextran Sulfate/150 mM MgCl) respectively. Alternatively, spreading layer 320 may be Polyether Sulfone (PES) 18/13 TW Hyphil. Alternatively, secondary separation layer 335 may be an LDL or HDL or any other analytes selectivity layer. In one configuration, secondary separation layer 335 may be an HDL fractionation layer including Deionized water 800.00 mL, Magnesium Sulfate 5.00 gm, Phosphotungstic Acid 45.00 gm, and Sorbitol 10.00 gm. The pH may be adjusted with NaOH or HCl pH 6.40-6.60. The volume may be adjusted to 1 liter with deionized water. Alternatively, separation layer 330 may be impregnated using a solution including Deionized water 800.00 mL, D-Sorbitol 75.00 gm, and Sodium Chloride 10.00 gm with the volume adjusted to 1 liter with deionized water. The focus of this disclosure is providing a dynamic range and not detecting a specific analyte, since many techniques are known for detecting specific analytes. The analyte detection membrane section 341, 342, 343 includes the chemistry described above, including different amounts of the moderator (GSS) to provide dynamic ranges. The above is only a small example of the possibilities for the chemistry and makeup of the layers.

Figure 4:
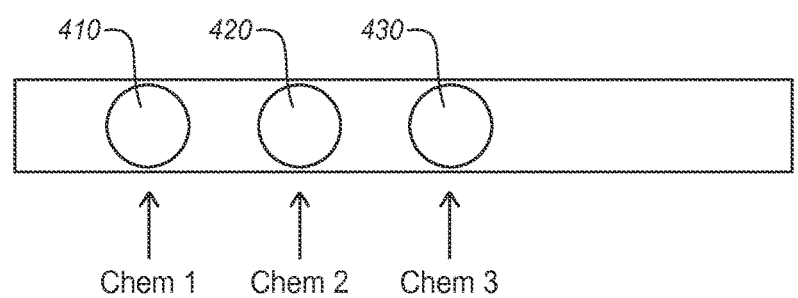
FIG. 4 shows the windows of the test strip of FIG. 3.

As shown in FIG. 4, the reaction membranes with different dynamic ranges then can be layered together with blood separation layers and introduced into a 3-analyte cell holder such that Chem 1 410 will contain a cholesterol membrane with a low dynamic range from 100-400 mg/dL, Chem 2 420 with an intermediate dynamic range of 400-800 mg/dL, and Chem 3 430 with a high dynamic range of 800-1400 mg/dL. The resulting panel test strip now will act like a single test strip capable of a dynamic range from 100-1400 mg/dL.

About 40 µL of whole blood can be applied to the test strip. The sample will be spread across the test strip using a blood spreading layer, and the red blood cells will be filtered using a blood separation layer, followed by the final reaction membrane to quantify the amount of cholesterol in the sample.

A meter such as a CardioChek Meter® may accompany such a test strip, where the meter will display the chemistry name and the values of the analyte.

The approach described above for cholesterol is not limited only to the cholesterol analyte. This chemistry can be exploited to any analyte like triglycerides, HDL Cholesterol, Glucose, Creatinine, and any other analyte where hydrogen peroxide is generated in the enzyme cascade.

Examples and Results:

Total Cholesterol formulations were prepared where reduced Glutathione (GSH) was titrated to target the low (100-400 mg/dL), moderate (400-800 mg/dL), and high (800-1400 mg/dL) cholesterol dynamic range.

Figure 5:
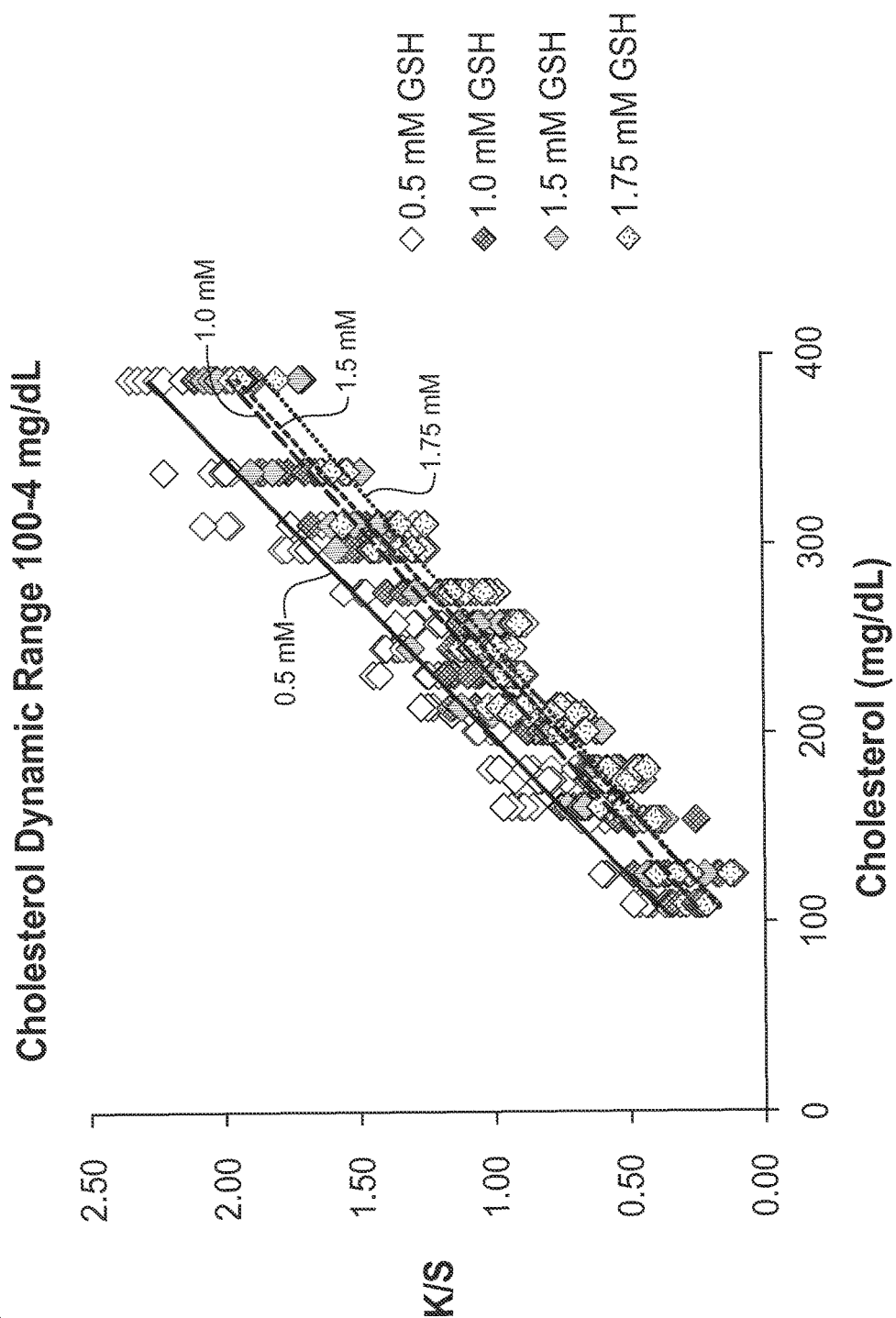
FIG. 5 shows a graph of a significant dose response between K/S vs. cholesterol concentration using an embodiment of a test strip employing dynamic ranges.

For a low dynamic (100-400 mg/dL) range, a variety of GSH concentrations were tested, and the optimal concentration was deemed to be at 1.5 mM. The formulation was coated onto a Biodyne A membrane and dried. The dried membrane was cast into test strips that contained a blood spreading layer and blood separation membrane(s). Whole blood with total cholesterol ranging from 100-400 mg/dL was dosed on the test strip and the percent of reflectance recorded. The percent of reflectance (R) was converted to K/S (where K and S are absorption and scattering coefficients, respectively) using the well-known Kubelka-Munk equation $\{K/S=(1-R)^2/2R\}$. The graph of FIG. 5 shows significant dose response between K/S vs. cholesterol concentration.

Figure 6:
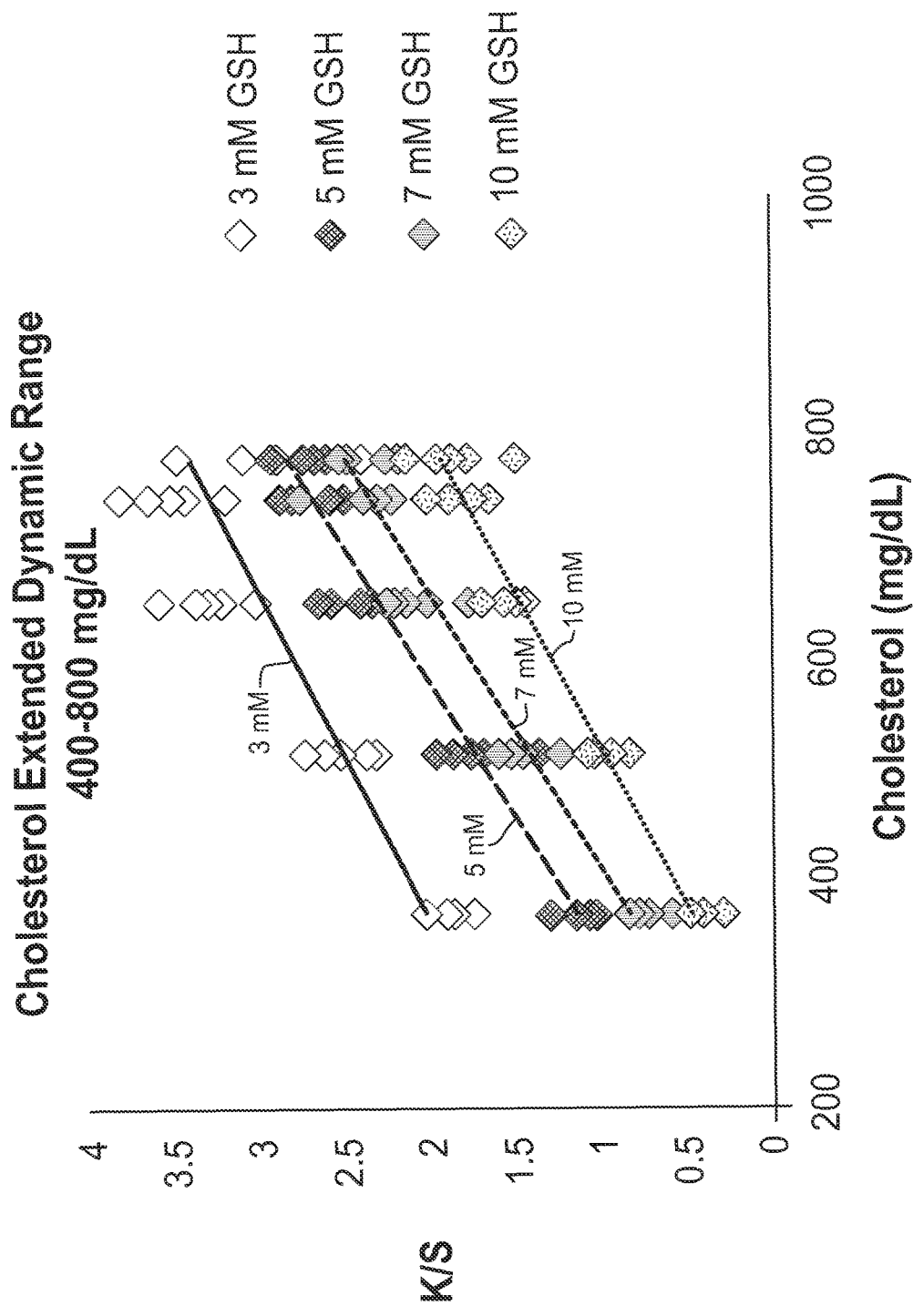
FIG. 6 shows a graph of a significant dose response between K/S vs. cholesterol concentration for all four levels of GSH employed using an embodiment of a test strip employing dynamic ranges.

For a moderate dynamic range (400-800 mg/dL), GSH was titrated between 3-10 mM in the cholesterol formulation. The formulation was coated onto a Biodyne A membrane and dried. The dried membrane was cast into test strips that contained a blood spreading layer and blood separation membrane(s). Whole blood with total cholesterol ranging from 400-800 mg/dL was dosed on the test strip and the percent of reflectance was recorded. The percent of reflectance was converted to K/S using the well-known Kubelka-Munk equation. The graph of FIG. 6 shows significant dose response between K/S vs. cholesterol concentration for all four levels of GSH employed.

Figure 7:
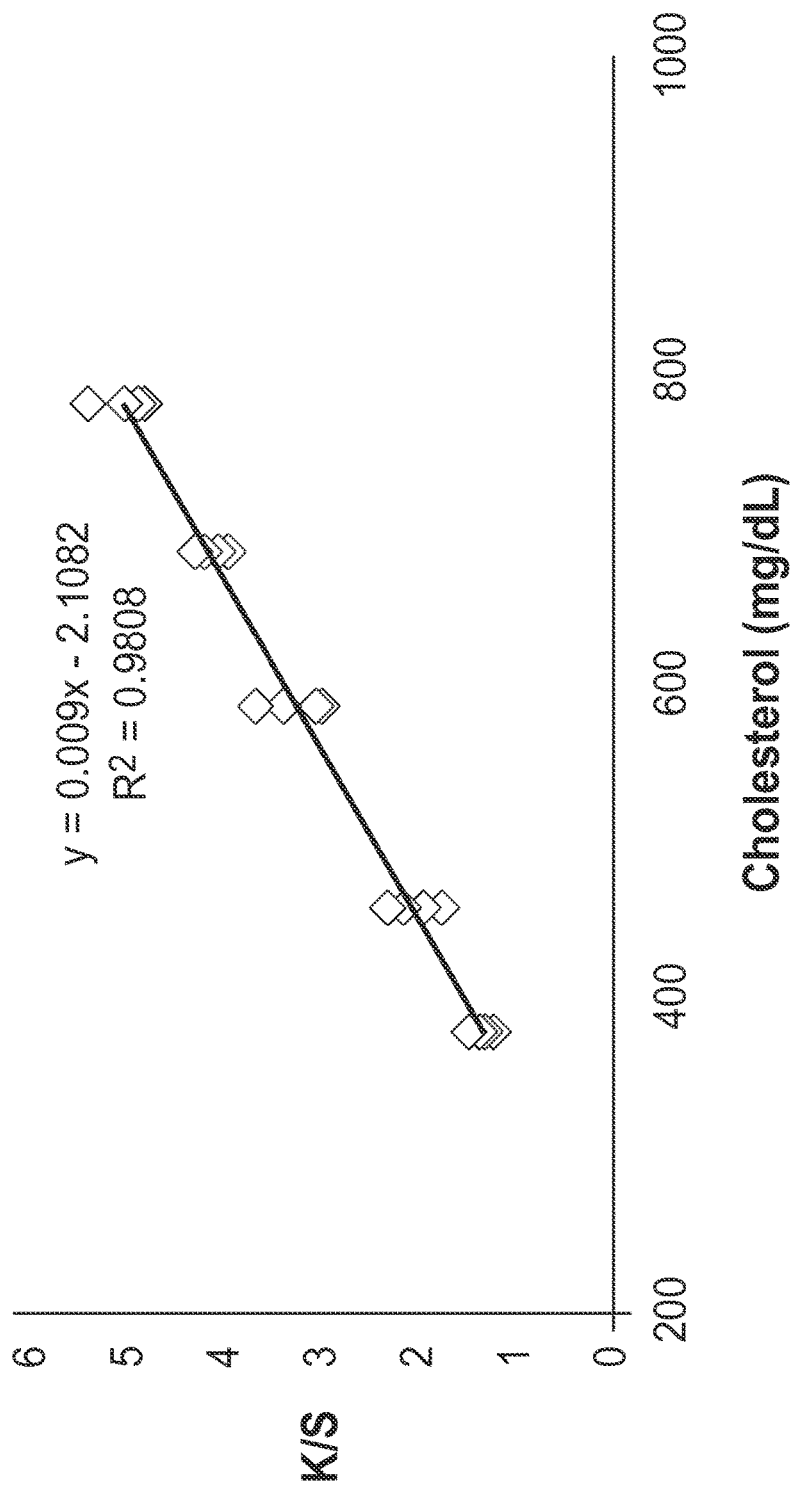
FIG. 7 shows a graph of excellent correlation indicating good precision at higher cholesterol values using an embodiment of a test strip employing dynamic ranges.

Of the four levels tested, 5 mM GSH concentration seemed to be an optimal concentration. This condition was further fine-tuned to increase the sensitivity of the test, using a new end point detection algorithm on the CardioChek Meter®. The graph of FIG. 7 shows excellent correlation indicating good precision at higher cholesterol values.

Figure 8:
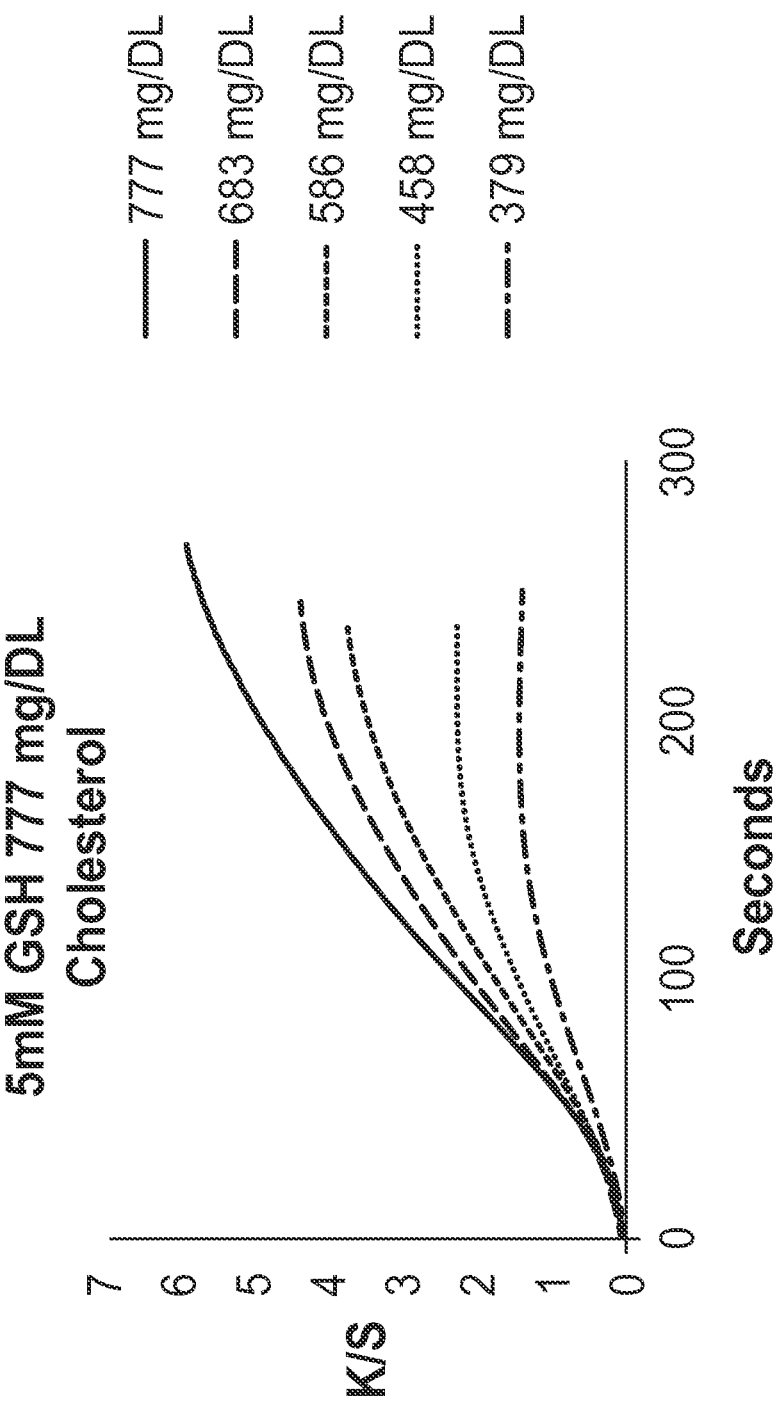
FIG. 8 shows a graph that shows when an embodiment of a test strip employing dynamic ranges is dosed with increasing concentrations of cholesterol in whole blood, a proportional increase in the kinetics is observed.

A kinetic study was performed to determine the nature of the dose response. The graph of FIG. 8 shows that when the test strip is dosed with increasing concentrations of cholesterol in whole blood, a proportional increase in the kinetics is observed, further confirming that the membrane is responding to the analyte and not displaying any non-specific reactions to a matrix interference.

Figure 9:
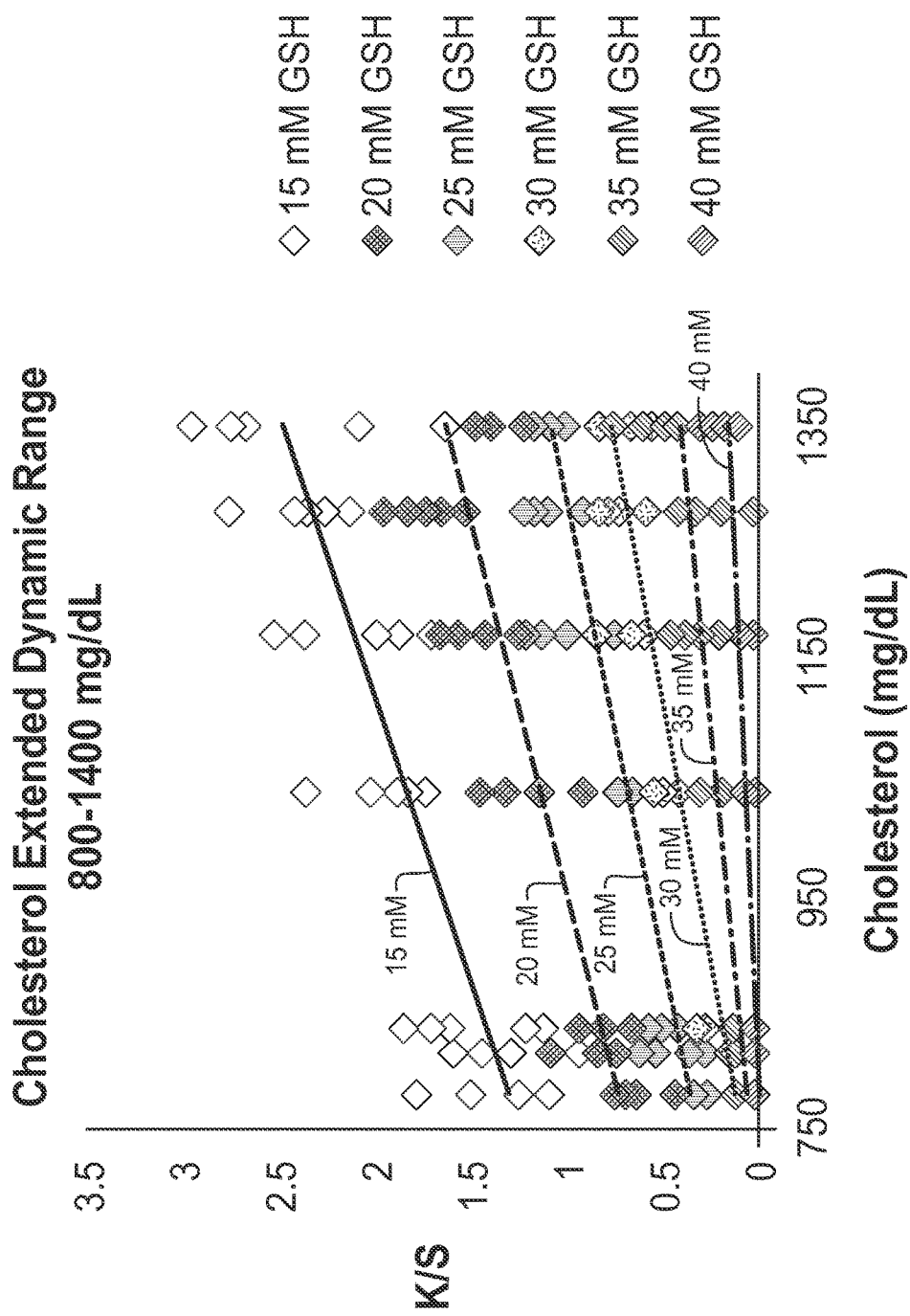
FIG. 9 shows a significant dose response between K/S vs. cholesterol concentration for all four levels of GSH employed using an embodiment of a test strip employing dynamic ranges.

Lastly, for a higher dynamic range (800-1400 mg/dL), GSH was titrated between 15-40 mM in the cholesterol formulation. The formulation was coated onto a Biodyne A membrane and dried. The dried membrane was cast into test strips that contained a blood spreading layer and blood separation membrane(s). Whole blood with total cholesterol ranging from 800-1400 mg/dL was dosed on the test strip and the percent of reflectance recorded. The percent of reflectance was converted to K/S using the well-known Kubelka-Munk equation. The graph of FIG. 9 shows a significant dose response between K/S vs. cholesterol concentration for all four levels of GSH employed.

The previous detailed description is of a small number of embodiments for implementing the systems and methods for creating test strips with extended dynamic ranges and the systems of test strips with extended dynamic ranges and is not intended to be limiting in scope. The following claims set forth a number of the embodiments of the systems and methods for creating test strips with extended dynamic ranges and the systems of test strips with extended dynamic ranges disclosed with greater particularity.

What is claimed:

1. A multirange test strip, the test strip comprising:
a sample;
a spreading layer, wherein the spreading layer is operable for spreading the sample across substantially the total length of the multirange test strip;
at least one analyte cell holder, the at least one analyte cell holder located vertically below the spreading layer;
a first analyte stack and a second analyte stack, the first and second analyte stacks, the first and second analyte stacks located vertically below the spreading layer and in fluidic communication with the spreading layer, the first and second analyte stacks having layers and reagents for testing for an analyte, the layers and reagents for testing for the analyte for the first and second analyte stacks being the same, wherein the second analyte stack includes a peroxide modulator, and the first analyte stack has a first dynamic range for the analyte and a first sensitivity and precision; and the second analyte stack has a second dynamic range corresponding to a first amount of the peroxide modulator added and a second sensitivity and precision, the second sensitivity and precision approximately equal to the first sensitivity and precision, wherein the analyte that the first analyte stack and the second analyte stack is the same.

2. The multirange test strip of claim 1, wherein the peroxide modulator is glutathione.

3. The multirange test strip of claim 2, wherein the analyte is cholesterol.

4. The multirange test strip of claim 3, wherein the layers and reagents for testing for an analyte include 4-Amino antipyrine (4-AAP) and N,N-disubstituted aniline derivatives which produce a colorimetric response.

5. The multirange test strip of claim 4, wherein when whole blood is added to the test strip, the glutathione reacts with hydrogen peroxide to produce glutathione disulfide.

6. The multirange test strip of claim 5, wherein the first range is 100-400 mg/dL, and the second range is 400-800 mg/dL.

7. The multirange test strip of claim 6, further comprising:
a third analyte stack, the third analyte stack in fluidic communication with the spreading layer, the third analyte stack having the layers and reagents for testing for the analyte, the layers and reagents for testing for the analyte for the first, second, and third analyte stacks being the same, wherein the third analyte stack includes the peroxide modulator, and the third analyte stack has a third dynamic range corresponding to a second amount of the peroxide modulator added and a third sensitivity and precision, the third sensitivity and precision approximately equal to the first sensitivity and precision.

8. The multirange test strip of claim 7, wherein the third range is 800-1400 mg/dL.

9. The system of claim 1, wherein each of the first and second analyte stacks include cholesterol detection chemistry, the cholesterol detection chemistry being the same for each of the first and second analyte stacks except for the first and second amounts of peroxide modulator.

10. The system of claim 1, wherein the first and second analyte stack produce a colorimetric response measurable with a meter.

11. The system of claim 1, further comprising a meter, the meter configured and executing instructions for reading the first and second analyte stacks and providing a calculated level of the analyte.

12. A multirange test strip, the test strip comprising:
a spreading layer;
a first analyte stack and a second analyte stack, the first and second analyte stacks in fluidic communication with the spreading layer, the first and second analyte stacks consisting of layers and reagents for testing for an analyte, the layers and reagents for testing for the analyte for the first and second analyte stacks being the same, wherein the second analyte stack additionally consists of a peroxide modulator, and the first analyte stack has a first dynamic range for the analyte and a first sensitivity and precision; and the second analyte stack has a second dynamic range corresponding to a first amount of the peroxide modulator added and a second sensitivity and precision, the second sensitivity and precision approximately equal to the first sensitivity and precision, wherein the analyte that the first analyte stack and the second analyte stack is the same.

13. A multirange test strip, the test strip comprising:
a spreading layer, wherein the spreading layer is operable for spreading a sample across substantially the total length of the multirange test strip;
at least one analyte cell holder, the at least one analyte cell holder located vertically below the spreading layer;
a first analyte stack and a second analyte stack, the first and second analyte stacks, the first and second analyte stacks located vertically below the spreading layer and in fluidic communication with the spreading layer, the first and second analyte stacks consisting of layers and reagents for testing for an analyte that produce a colorimetric response to the analyte allowing the analyte to be measured, the layers and reagents for testing for the analyte for the first and second analyte stacks being the same, wherein the second analyte stack additionally consists of a peroxide modulator, and the first analyte stack has a first dynamic range for the analyte and a first sensitivity and precision; and the second analyte stack has a second dynamic range corresponding to a first amount of the peroxide modulator added and a second sensitivity and precision, the second sensitivity and precision approximately equal to the first sensitivity and precision, wherein the analyte that the first analyte stack and the second analyte stack is the same.

14. The multirange test strip of claim 1, wherein the first and second analyte stacks having layers and reagents for testing for the analyte produce a colorimetric response to the analyte allowing the analyte to be measured.

15. The multirange test strip of claim 12, wherein the first and second analyte stacks having layers and reagents for testing for the analyte produce a colorimetric response to the analyte allowing the analyte to be measured.

* * * * *